(12) United States Patent
Stefanov

(10) Patent No.: US 11,951,287 B2
(45) Date of Patent: Apr. 9, 2024

(54) PNEUMATIC POWER PACK

(71) Applicant: SHL MEDICAL AG, Zug (CH)

(72) Inventor: Slobodan Stefanov, Deerfield Beach, FL (US)

(73) Assignee: SHL MEDICAL AG, Zug (CH)

(*) Notice: Subject to any disclaimer, the term of this patent is extended or adjusted under 35 U.S.C. 154(b) by 756 days.

(21) Appl. No.: 16/972,504

(22) PCT Filed: Sep. 12, 2019

(86) PCT No.: PCT/EP2019/074299
§ 371 (c)(1),
(2) Date: Dec. 4, 2020

(87) PCT Pub. No.: WO2020/058068
PCT Pub. Date: Mar. 26, 2020

(65) Prior Publication Data
US 2021/0268193 A1 Sep. 2, 2021

Related U.S. Application Data

(60) Provisional application No. 62/735,047, filed on Sep. 22, 2018.

(30) Foreign Application Priority Data

Nov. 8, 2018 (EP) .................................. 18205275

(51) Int. Cl.
*A61M 5/20* (2006.01)
*A61M 5/32* (2006.01)

(52) U.S. Cl.
CPC ........ *A61M 5/2053* (2013.01); *A61M 5/3243* (2013.01); *A61M 2205/8225* (2013.01)

(58) Field of Classification Search
CPC .. A61M 5/2053; A61M 5/2046; A61M 5/155; A61M 2205/8225
See application file for complete search history.

(56) References Cited

U.S. PATENT DOCUMENTS 2,605,763 A    8/1952   Smoot
3,688,765 A *   9/1972   Gasaway ................ A61M 5/30
                                                             124/71

(Continued)

FOREIGN PATENT DOCUMENTS

CN           1909939 A     2/2007
JP        2017-519580 A     7/2017

(Continued)

OTHER PUBLICATIONS

International Search Report and Written Opinion for Int. App. No. PCT/EP2019/074299, dated Nov. 15, 2019.

*Primary Examiner* — Emily L Schmidt
(74) *Attorney, Agent, or Firm* — McDonnell Boehnen Hulbert & Berghoff LLP

(57) ABSTRACT

A pneumatic power pack for a medicament delivery device is presented having a pressurized gas container storing pressurized gas and an activation assembly for releasing the pressurized gas from the gas source. The activation assembly including a rupturer having a sharp end, an activator, and a rotator coupled with the activator and the gas container. The activator is configured to move from a first position toward a second position to causes a rotation of the rotator which then drives the gas source towards the sharp end of the rupturer to release the pressurized gas.

11 Claims, 13 Drawing Sheets

(56) References Cited

U.S. PATENT DOCUMENTS

| | | | |
|---|---|---|---|
| 4,790,824 A * | 12/1988 | Morrow | A61M 5/30 604/143 |
| 5,312,335 A | 5/1994 | McKinnon et al. | |
| 2005/0267403 A1* | 12/2005 | Landau | A61M 5/30 604/70 |
| 2012/0035538 A1 | 2/2012 | Elmen et al. | |
| 2016/0361496 A1 | 12/2016 | Guillermo et al. | |
| 2018/0008775 A1 | 1/2018 | Stefanov | |

FOREIGN PATENT DOCUMENTS

| | | |
|---|---|---|
| WO | 2013/086612 A1 | 6/2013 |
| WO | 2013/182859 A1 | 12/2013 |
| WO | 2015/197867 A1 | 12/2015 |
| WO | 2018/011255 A1 | 1/2018 |

* cited by examiner

PNEUMATIC POWER PACK

CROSS REFERENCE TO RELATED APPLICATIONS

The present application is a U.S. National Phase Application pursuant to 35 U.S.C. § 371 of International Application No. PCT/EP2019/074299 filed Sep. 12, 2019, which claims priority to U.S. Provisional Patent Application No. 62/735,047 filed Sep. 22, 2018, and European Patent Application No. 18205275.3 filed Nov. 8, 2018. The entire disclosure contents of these applications are herewith incorporated by reference into the present application.

TECHNICAL AREA

The present disclosure relates to a pneumatic power pack and in particular to a pneumatic power pack for a medicament deliver device.

BACKGROUND

Unless otherwise indicated herein, the materials described in this section are not prior art to the claims in this application and are not admitted to be prior art by inclusion in this section.

In some situations, it is desirable for patients to be able to administer drugs and medicament by themselves, e.g., without the need for trained medical staff to administer the drugs. There are a number of different existing delivery devices with varying degrees of automatic functions. For instance, existing automatic injection devices provide means for automatically propelling a plunger forward to eject medicament from the automatic injection device in response to activation of the device.

In existing devices, the means for automatically propelling the plunger forward to eject the medicament are often complex and expensive to manufacture. Further, for some types of medicaments, there is a desire to eject the medicament at a substantially constant force. However, certain existing devices for ejecting the medicament at a substantially constant force are complex and expensive to manufacture. There is, therefore, a desire to reduce the cost of manufacturing automatic injection devices while maintaining the reliability of the injection device to eject a dose of medicament.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

These and other aspects of, and advantages with, the present disclosure will become apparent from the following detailed description of the present disclosure and from the accompanying drawings.

According to a main aspect of the disclosure it is characterized by a pneumatic power pack for a medicament delivery device. The pneumatic power pack comprises a pressurized gas container storing pressurized gas and an activation assembly for releasing the pressurized gas from the gas source. The activation assembly including a rupturer having a sharp end, an activator, and a rotator coupled with the activator and the gas container. The activator is configured to move from a first position toward a second position to causes a rotation of the rotator which then drives the gas source towards the sharp end of the rupturer to release the pressurized gas.

In other embodiments, the activation assembly further includes a retainer coupled with the rotator, the gas container is arranged in the retainer, the axial movement of the activator causes a rotation of the rotator which then drives the retainer and the gas source towards the sharp end of the rupturer. The activation assembly further includes a first bracket coupling with the retainer, the coupling between the first bracket and retainer transforms the biased movement of the retainer from rotational to longitudinal. The first bracket has a passageway for accommodating the rupturer and at least part of the gas source, a flow of the pressurized gas travels from the gas source through the rupturer and exits from the passageway. The pneumatic power pack further comprises second bracket and a valve disposed in the second bracket, wherein the valve receives a flow of gas exiting the passageway of the first bracket.

Further, the activator includes a first member and the rotator includes a second member configured to engage the first member. The first member is configured to interact with the second member during the axial movement of the activator from the first position to the second position to rotate the rotator. In one embodiment, the first member is arranged on an inner surface of the activator, the second member is arranged on an outer surface of the rotator. In another embodiment, the first protrusion is arranged on an outer surface of the activator, the first trough is arranged on an inner surface of the rotator.

In addition, the rotator includes a third member and the retainer includes a fourth member configured to engage the third member, the third member is configured to interact with the fourth member during the rotation of the rotator to drive the gas source. In other embodiments, the rotator has a first fixing member and the retainer has a second fixing member configured to engage the first fixing member to maintain a position of the rotator before being rotated by the activator moving from the first position to the second position.

BRIEF DESCRIPTION OF DRAWINGS

In the following detailed description of the present disclosure, reference will be made to the accompanying drawings, of which

DETAILED DESCRIPTION

Figure 1:
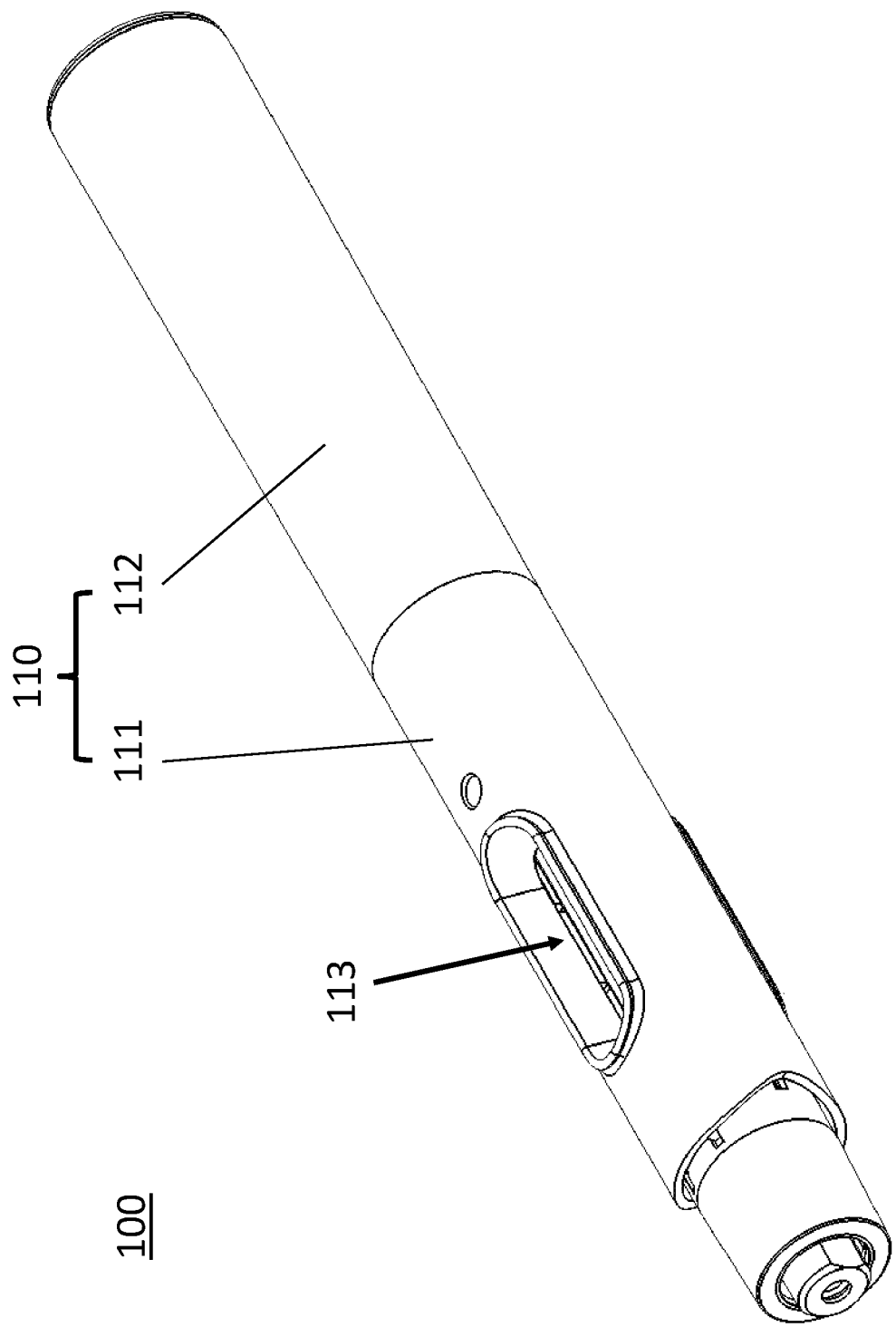
FIG. 1 shows a perspective view of an example medicament delivery device according to a first embodiment of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The methods and systems in accordance with the present disclosure beneficially provide improved methods and systems for propelling a plunger forward so as to eject the medicament from an automatic injection device. The disclosed methods and systems provide a reliable, intuitive, and user-friendly drug delivery device that uses a pressurized gas to eject a dose of medicament. Further, the disclosed methods and systems provide a cost effective means for propelling the plunger forward so as to eject the medicament and thus help to reduce the cost of manufacturing automatic injection devices.

FIG. 1 generally illustrates an example drug delivery device that uses pressurized gas to deliver a dose of medicament. In particular, FIG. 1 illustrates a drug delivery device 100 in an initial state prior to injection. Further, FIG. 2 illustrates an exploded view of the components of the drug delivery device 100 in the initial state prior to injection.

Figure 2:
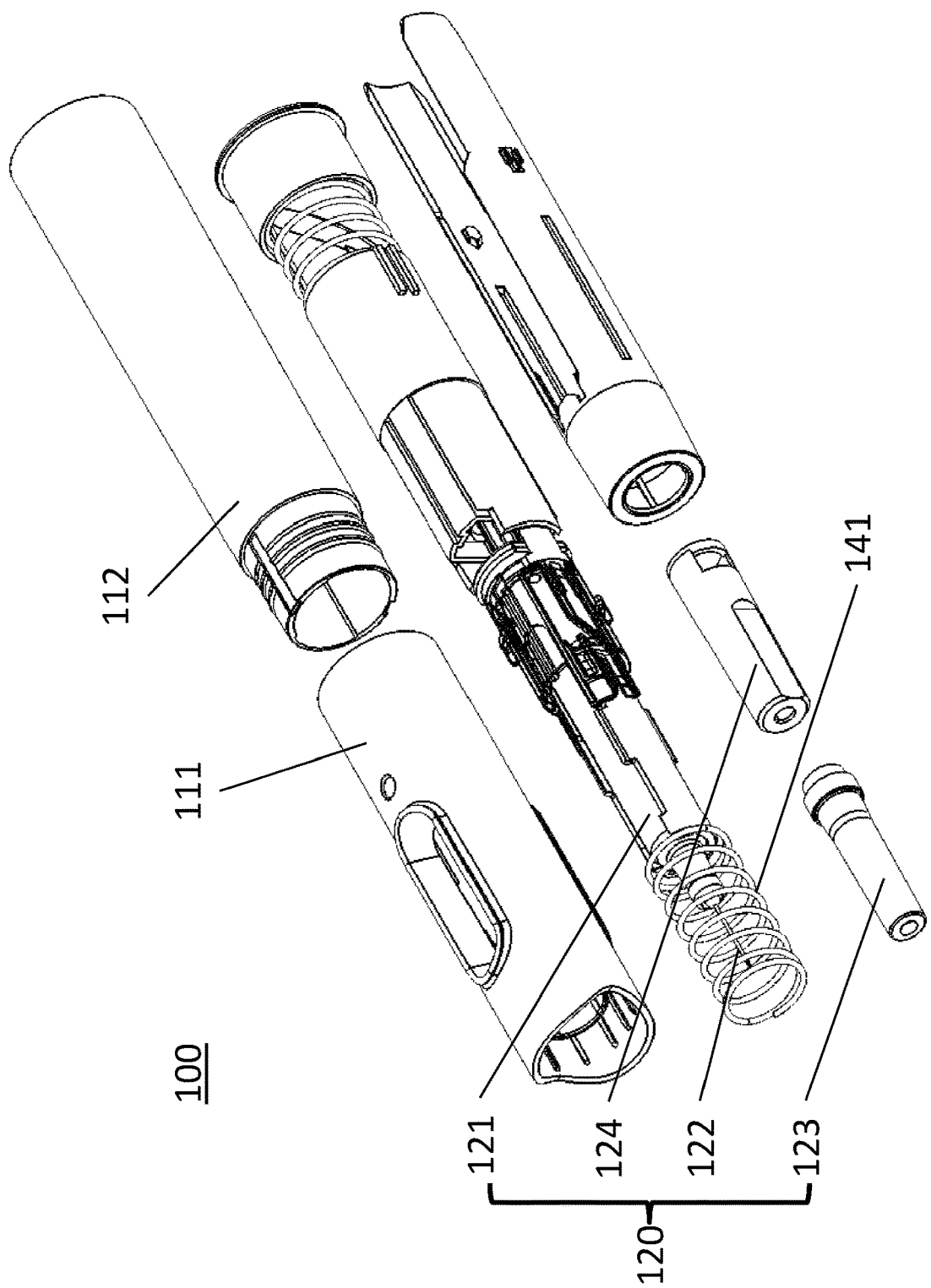
FIG. 2 shows an exploded view of an example medicament delivery device according to a first embodiment of the present disclosure.

As seen in FIGS. 1 and 2, drug delivery device 100 includes a main housing 110 and a syringe 120 arranged in the main housing 110. Main housing 110 includes a first housing portion 111 and a second housing portion 112. The first and second housing portions 111, 112 include corresponding engagement features for providing an engagement between the two housing portions 111, 112. In an example embodiment, during assembly of the drug delivery device 100, the first and second housing portions 111, 112 are irreversibly attached to one another. However, in other embodiments, the housing portions 111, 112 can also be reversibly attached to each other. Although main housing 110 is depicted as comprising first and second housing portions 111, 112, in other examples, main housing 110 may comprise more or fewer portions. For instance, in an example embodiment, main housing 110 can be of unitary construction. With reference to FIG. 2, the syringe 120 includes a syringe body 121 holding a medicament, a needle 122, and a first and second needle cover 123, 124 covering the needle 122. A piston or stopper (not illustrated) is disposed in the syringe body 121. The rest of the components are part of a pneumatic power pack 130 that will be further explained in details below. Additionally or alternatively, the piston/stopper in the syringe body 121 and plunger 150 may be visible in the main body window 113 (see FIG. 1) when injection is complete. In such an example, the end of delivery may be indicated by the piston and plunger 150 having stopped moving. Other indications of dose delivery being complete are possible as well.

Figure 3:
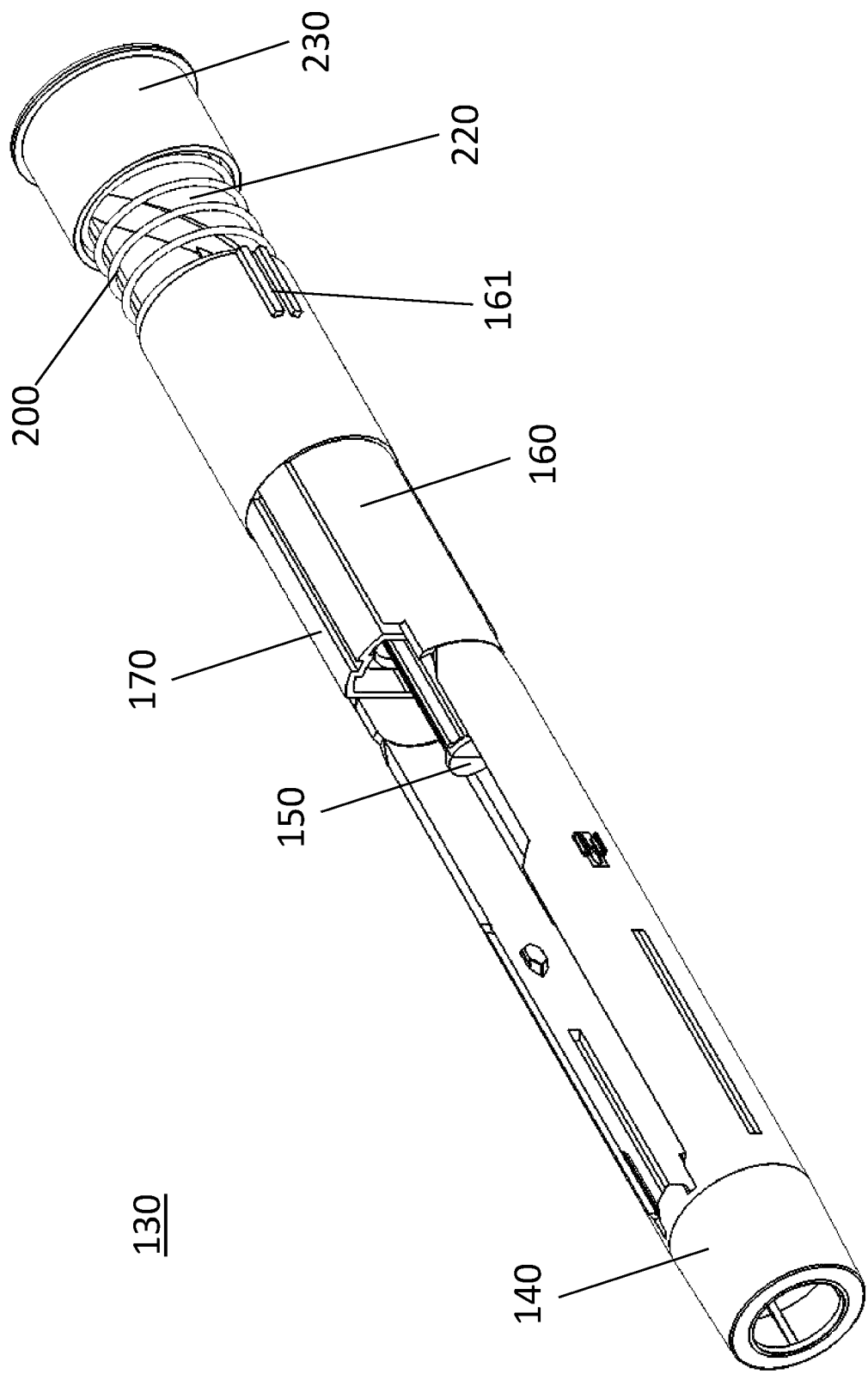
FIG. 3 shows a perspective view of an example pneumatic power pack according to a first embodiment of the present disclosure.
Figure 4:
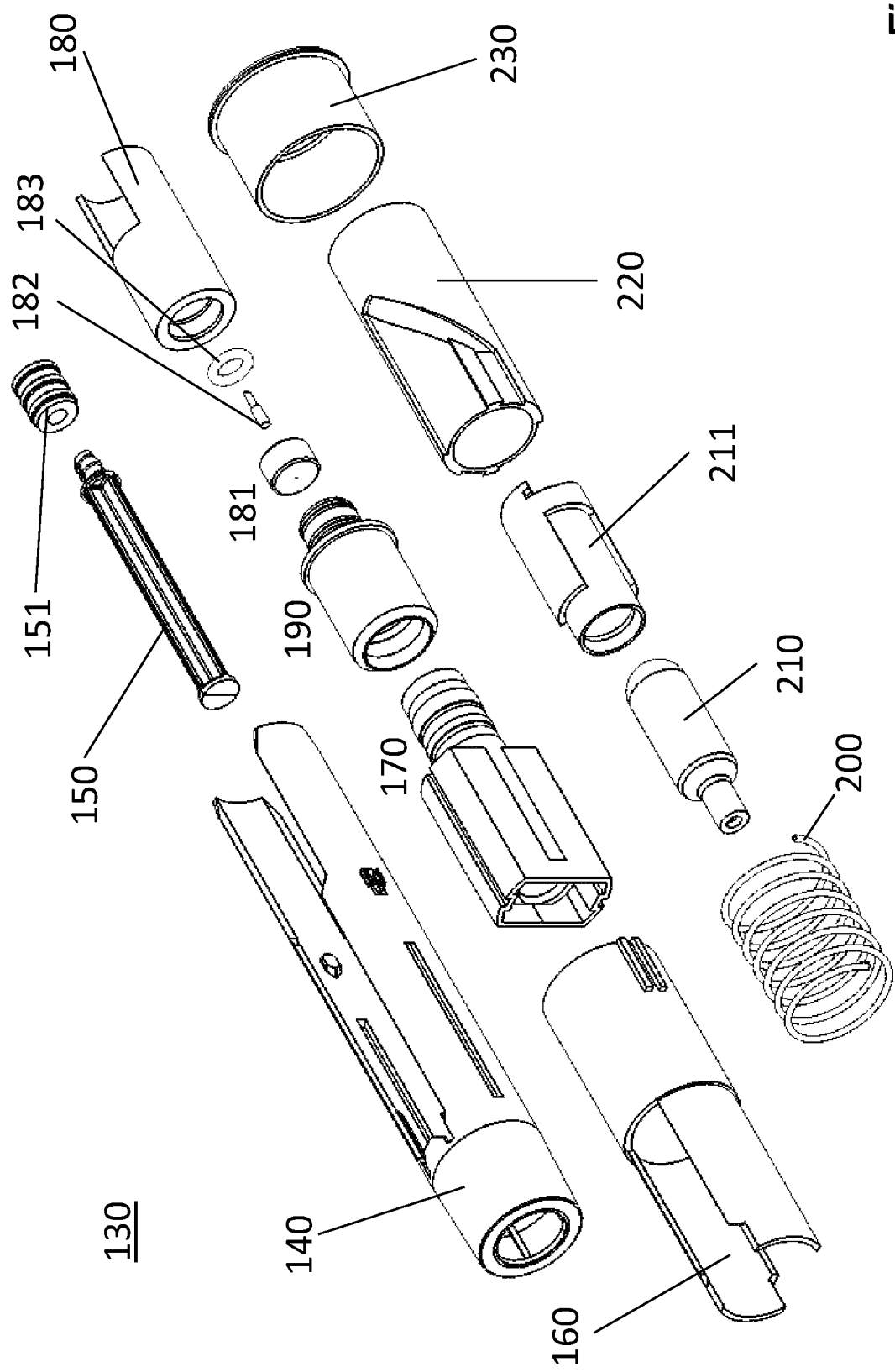
FIG. 4 shows an exploded view of an example pneumatic power pack according to a first embodiment of the present disclosure.

With reference to FIGS. 3-4, the drug delivery device 100 further includes a pneumatic power pack 130 for ejecting medicament from the syringe 120 through the needle 122. The pneumatic power pack 130 includes a needle shield 140, a plunger 150, a plunger stopper 151, a first rotator 160, a plunger carrier 170, a first bracket 180, an orifice 181, a rupturer 182, a washer 183, a second bracket 190, a second spring 200, a gas source 210, a gas source retainer 211, a second rotator 220, and a rear cap 230. In this example, the second housing portion 112 has an opening (not illustrated) on its distal end and the rear cap 230 is coupled with the distal end of the second housing portion 112 to cover the opening.

As illustrated in FIG. 3, the distal end of the needle shield 140 is in contact with the proximal end of the first rotator 160. Thus, when the needle shield 140 is pressed on the injection site, the force in the distal direction can be transferred from the needle shield 140 to the first rotator 160. This results in both the needle shield 140 and first rotator 160 moving together in the distal direction. The first spring 141 (illustrated in FIG. 2) is placed between the inner surface of the first housing portion 111 and that of the needle shield 140. The first housing portion 111 remained immobile and the needle shield 140 is movable in a longitudinal direction along the axis of the drug delivery device 100. Thus, when pressed against the injection site, the needle shield 140 moving in a distal direction will compress the first spring 141. Thus, when user removes the drug delivery device 100 from the injection site, the first spring 141 then is allowed to expand to move the needle shield 140 in a proximal direction. On the other hand, the second spring 200 is placed between the distal end of the first rotator 160 and the inner surface of the rear cap 230. The second spring 200 is used to absorb at least a portion of the force applied on the first rotator 160 from the needle shield 140. Thus, the first spring 141 and the second spring 200 are working together to make sure that forces created during random events such as a drop or transportation will not be strong enough to push both the needle shield 140 and first rotator 160 in a distal direction and accidentally activate the pneumatic power pack 130.

Figure 7:
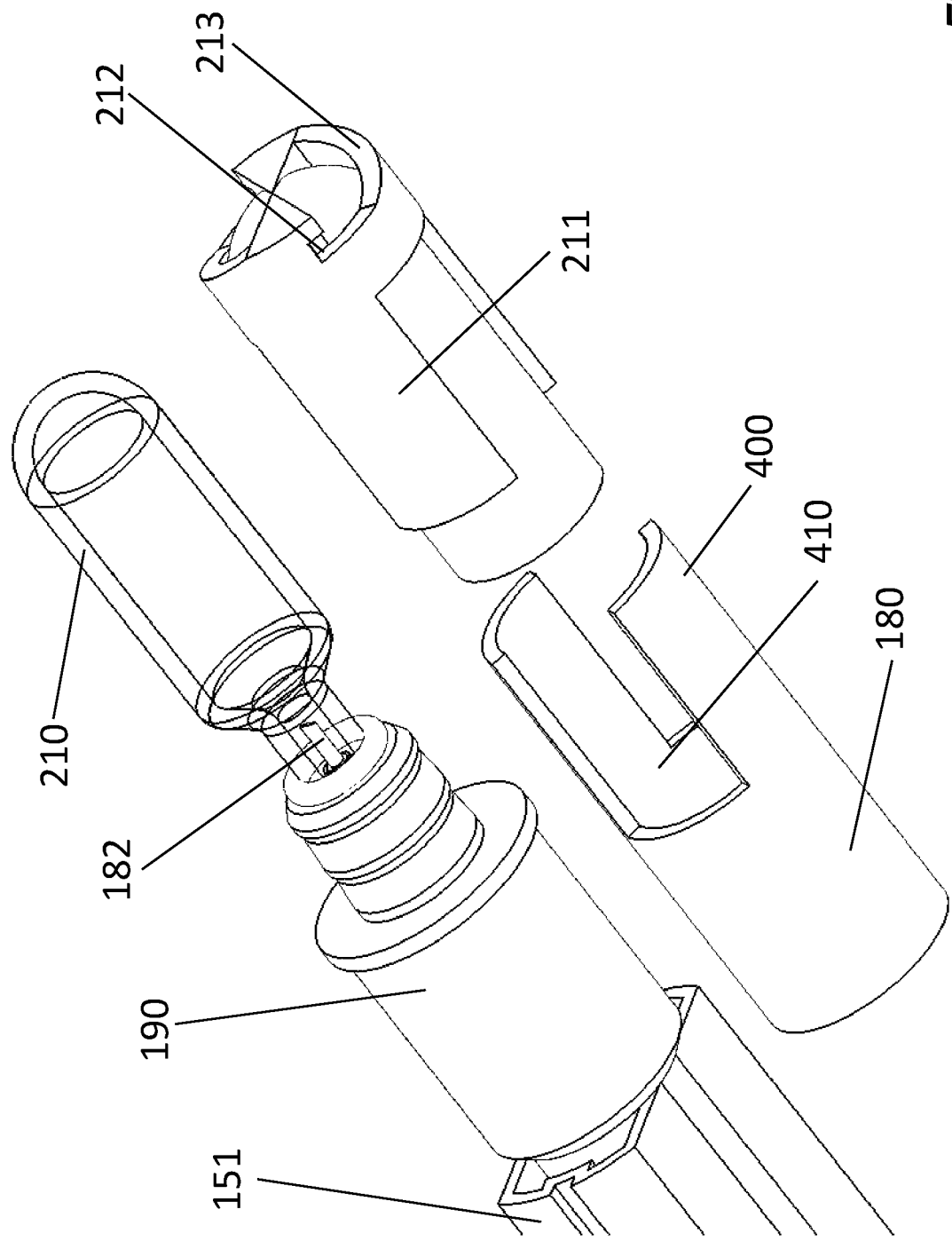
FIG. 7 shows a perspective view of the gas source, rupturer, second bracket, and plunger carrier.

As illustrated in FIG. 4, the gas source retainer 211 has a tubular shape with its inner space used to accommodate the gas source 210. In this example, the gas source 210 is a metallic canister storing pressurized gas and having a seal (not illustrated) to be ruptured in order to release the pressurized gas through the ruptured opening on the seal. The gas source retainer 211 in turn is placed in the inner space of the tubular second rotator 220. The gas source retainer 211 is to be coupled with the first bracket 180 as illustrated in FIG. 7. The first bracket 180 has a pair of arms 400 extending from the first bracket's 180 distal end and a pair of cut-outs 410 are formed between these arms 400. On the other hand, a portion of the gas source retainer 211 proximal end is carved out in order to accommodate the arms 400. Also, the protrusion of the gas source retainer 211 next to said carved-out can be fitted in the cut-outs 410. This configuration between the first bracket 180 and gas source retainer 211 ensures that the gas source retainer 211 can move only in a substantially longitudinal direction relative to the axis of the drug delivery device 100. The interaction between the first bracket 180 and gas source retainer 211 will be further explained below.

Pressurized gas source 210 may be any source of pressurized gas suitable to propel the plunger 150 forward to eject the medicament within the syringe 120. In an example embodiment, the pressurized gas is $CO_2$, Argon, or Nitrogen. Other example pressurized gases are possible as well. Further, in an example embodiment, the pressurized gas source 210 contains a gas pressurized to a pressure of between 50-3000 PSI. However, in other examples, the pressure may be less than 600 PSI or more than 3000 PSI. For instance, in another example, the pressure is between 500-600 PSI. In yet another example, the pressure is between 3000-3500 PSI. Other example pressures are possible as well.

In this example, the rupturer 182 is fixed in the inner space within the neck of the second bracket 190. The washer 183 is placed within the inner space of the first bracket 180 and is used to surround the neck of the gas source 210 to ensure an gas-tight engagement with the gas source 210. As used herein, "gas-tight engagement" means an engagement providing a seal that prevents or substantially prevents leakage of gas through the seal during the dose delivery process. By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide. Also, the neck on the distal side of the second bracket 190 is configured to couple with the proximal portion of the first bracket 180.

The orifice 181 is placed within the inner space on the distal portion of the plunger carrier 170 and is configured to ensure a gas-tight engagement with the plunger carrier 170. See FIG. 9. The orifice 181 has two openings respectively on its opposite proximal and distal ends so that the pressurized gas from the rupturer 182 can pass through the opening on the distal end and exit the orifice 181 through the opening on its proximal end.

The plunger stopper 152 and at least a portion of the plunger 150 are placed within the plunger carrier 170. See FIG. 9. The plunger stopper 152 is coupled with the distal portion of the plunger 150 so that they are movable together along a longitudinal direction. The pressurized gas exiting the orifice 181 will push both the plunger stopper 152 and plunger 150 to move in the proximal direction. The plunger stopper 152 also ensure an gas-tight engagement with the inner surface of at least the neck portion of the plunger carrier 170, to minimise the leakage of pressurized gas pushing the plunger stopper 152.

Above is a summary of the components and interactions between them. These interactions will be explained in more details with the figures that follow.

Figure 5:
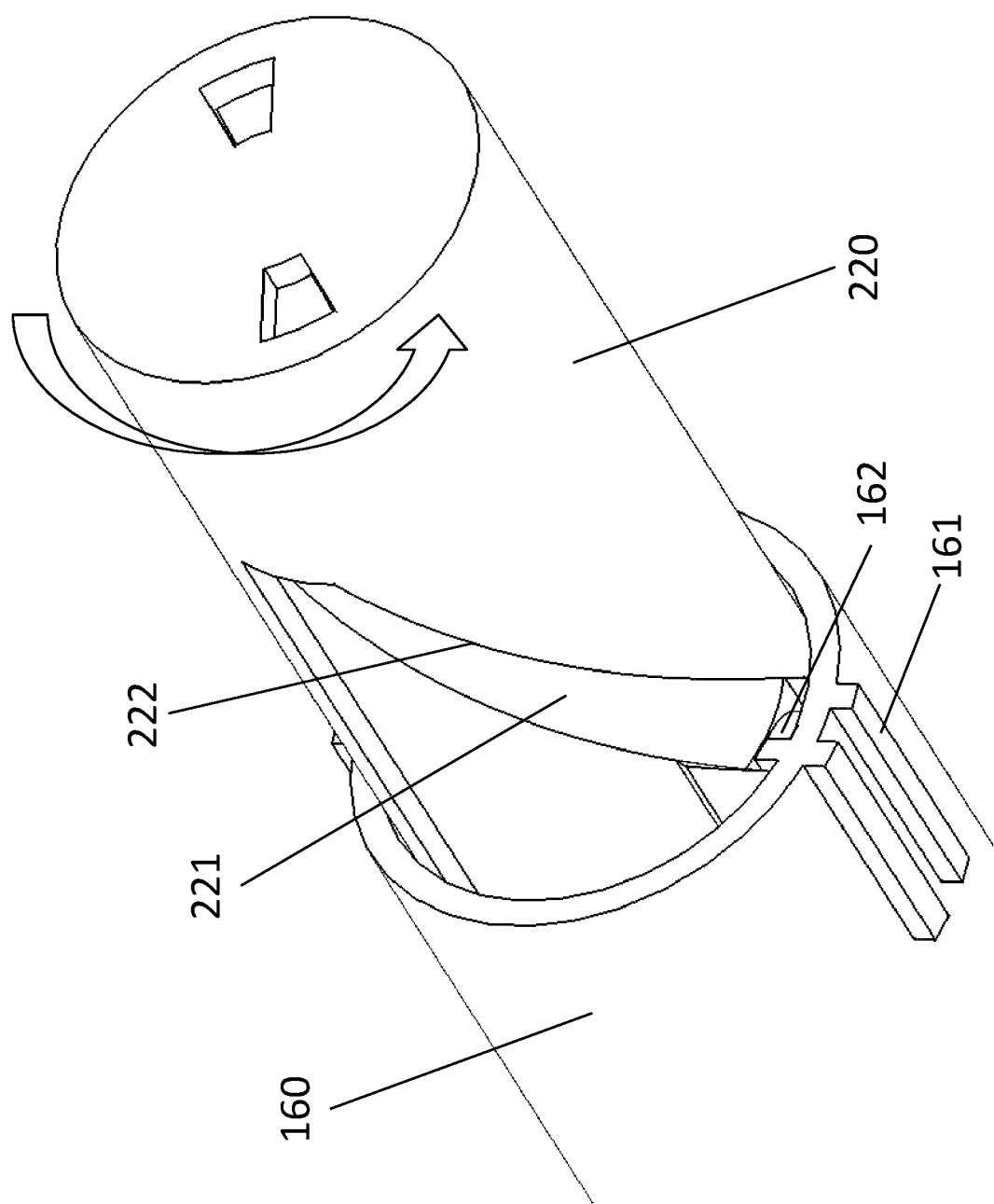
FIG. 5 shows a perspective view of the first and second rotators according to a first embodiment of the present disclosure.

Here please refer to both FIGS. 3 and 5 for the explanation on the interaction between the needle shield 140, first rotator 160, and second rotator 220. The first step to activate the pneumatic power pack 130 is to press the proximal end of needle shield 140 against an injection site. The needle shield 140 is longitudinally movable within the first housing portion 111. Thus, the reactional force from the injection site pushes the needle shield 140 to move in a distal direction. As the needle shield 140 moves in a distal direction, its distal end makes contact with the proximal end of first rotator 160 and also pushes the first rotator 160 to also move in the distal direction. As illustrated in FIGS. 3 and 5, the first rotator 160 includes two pairs of first protrusions 161 disposed on two opposite sides of the first rotator's 160 distal end. The first protrusions 161 are configured to couple with the troughs (not illustrated) disposed on the inner surface of the second housing portion 112. The first protrusions 161 and the corresponding troughs extend along a longitudinal direction and are parallel to the axis of the drug delivery device 100. This prevents the first rotator 160 from being rotated by forces from the needle shield 140 in the distal direction. In other words, the needle shield 140 and first rotator 160 are configured to move in the longitudinal direction with respect to the axis of the drug delivery device 100.

FIG. 5 shows a perspective view of the first and second rotators 160, 220. As illustrated in FIG. 5, the first rotator 160 further includes a pair of second protrusions 162 disposed on the inner surface of the first rotator's 160 distal end. On the other hand, a portion of the second rotator's 220 is carved out to create a trough 221 to accommodate the second protrusions 162. The trough 221 is oblique relative to the axis of the drug delivery device 100 and has a slant wall 222 configured to make contact with the second protrusions 162 during the longitudinal movement of the first rotator 160. As discussed above, the needle shield's 140 movement in the distal direction also forces the first rotation 160 to move in the distal direction. Also, the coupling between the first protrusions 161 of first rotator 160 and inner surface of the second housing portion 112 forces the first rotator 160 to only move in a longitudinal direction. Thus, as the first rotator 160 moves in the distal direction, its second protrusion 162 will collide with the slant wall 222 and force the second rotator 220 to rotate in a counter-clockwise direction as indicated by the arrow in FIG. 5.

Figure 6:
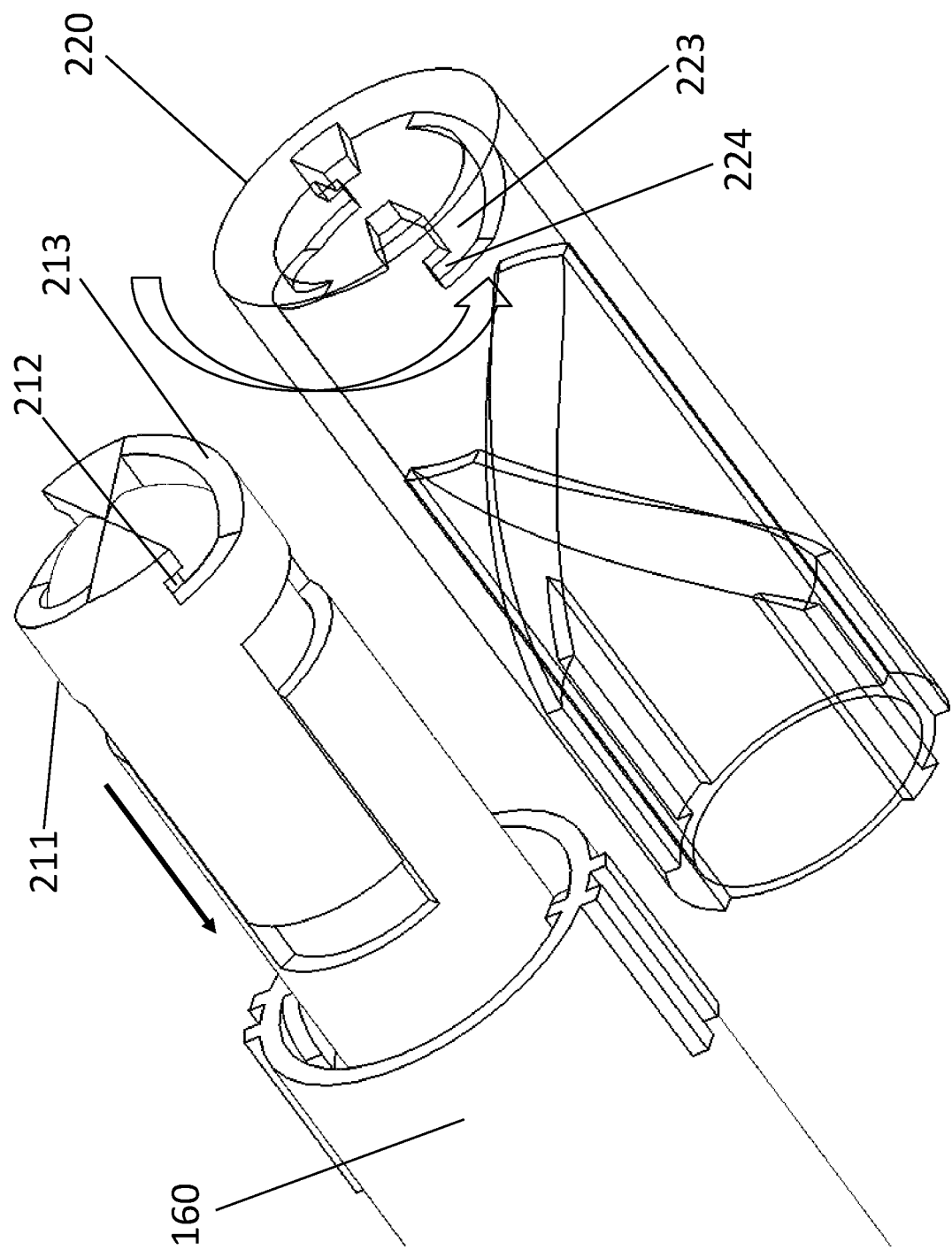
FIG. 6 shows a perspective view of the first rotator, second rotator, gas source retainer, and first bracket according to a first embodiment of the present disclosure.

FIG. 6 is a perspective showing the first rotator 160, second rotator 220, gas source retainer 211, and first bracket 180, wherein the second rotator 220 is made transparent to illustrate its inner structure. As illustrated, the second rotator 220 has a pair of third protrusions 223 extending from its inner surface. Each third protrusion 223 has a fixing members 224 configured to couple with the gas source retainer 211 before the second rotator 220 is rotated. The gas source retainer 211 has a pair of gaps 212 configured to accommodate the fixing members 224 in order to couple with the second rotator 220 before being rotated by the first rotator 160. The gas source retainer 211 also has a pair of slant slopes 213 corresponding to the third protrusions 223. Before the second rotator 220 is rotated, the third protrusion 223 simply rests on the slant slope 213 while the fixing member 224 is fitted in the gap 212. However, as the first rotator 160 forces to the second rotator 220 to rotate in a counter-clockwise direction, the fixing member 224 decouples from the gap 212. Also, the third protrusion 223 start colliding with the slant slope 213 and in the process pushes the entire gas source retainer 211 to move in a proximal direction.

As discussed above, the cut-outs 410 (illustrated in FIG. 7) of the first rotator 160 restricts the movement of the second rotator 220 to be along a substantially longitudinal direction. Further, the gas source 210 is placed within the gas source retainer 211 and these two component move together in the same direction. Accordingly, the rotation of the first rotator 160 and that of the second rotator 220 result in the movement of the gas source 210 and gas source retainer 211 in a proximal direction toward the rupturer 182 within the second bracket 190. As FIG. 7 shows, the rupturer 182 then pierce the seal of the gas source 210 to release the pressurized gas within. The pressurized gas then passes through the sharp end of the tubular rupturer 182 and exits through the opening at the opposite end.

Figure 8:
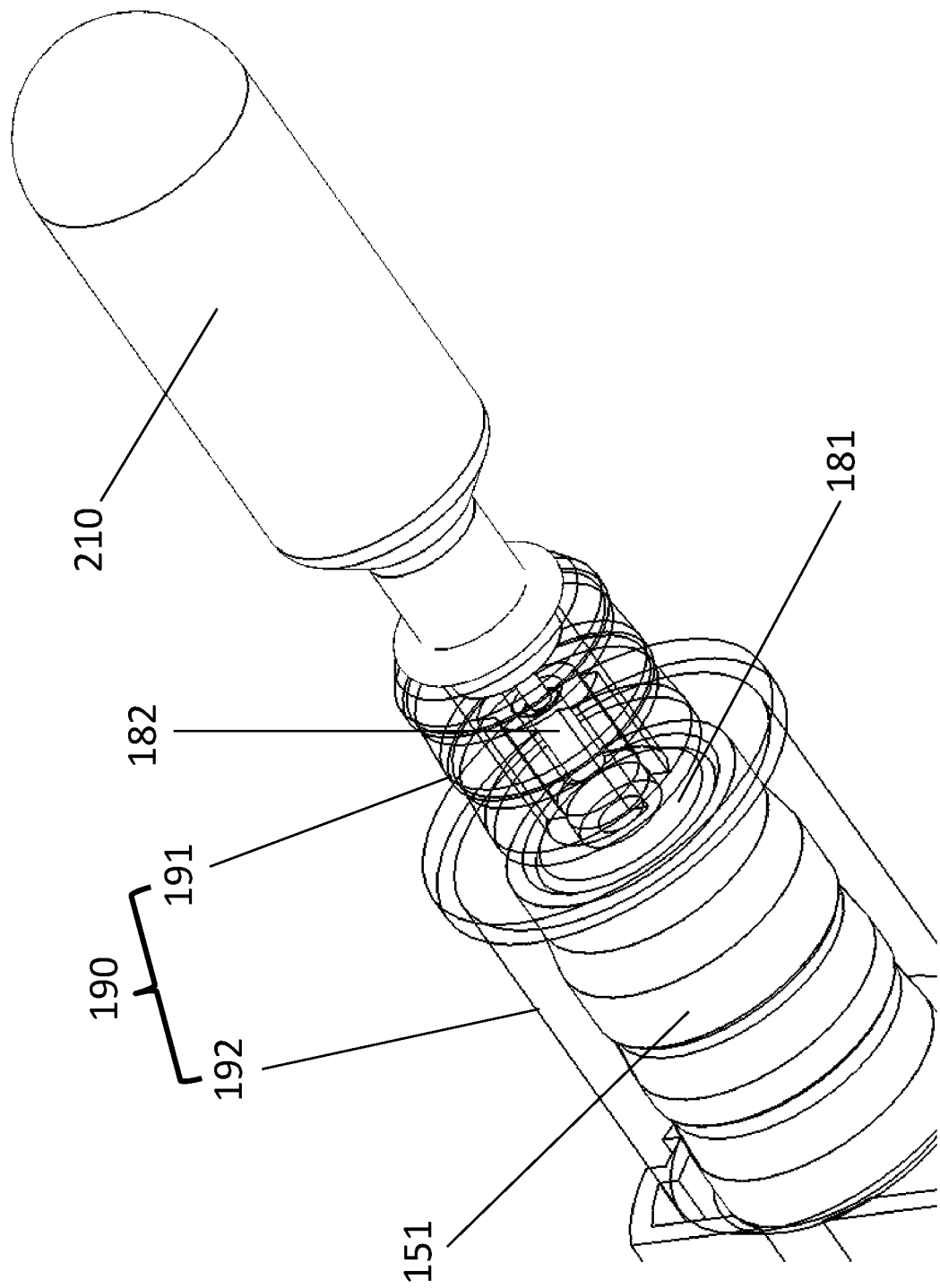
FIG. 8 shows another perspective view of the gas source, rupturer, second bracket, and plunger carrier.
Figure 9:
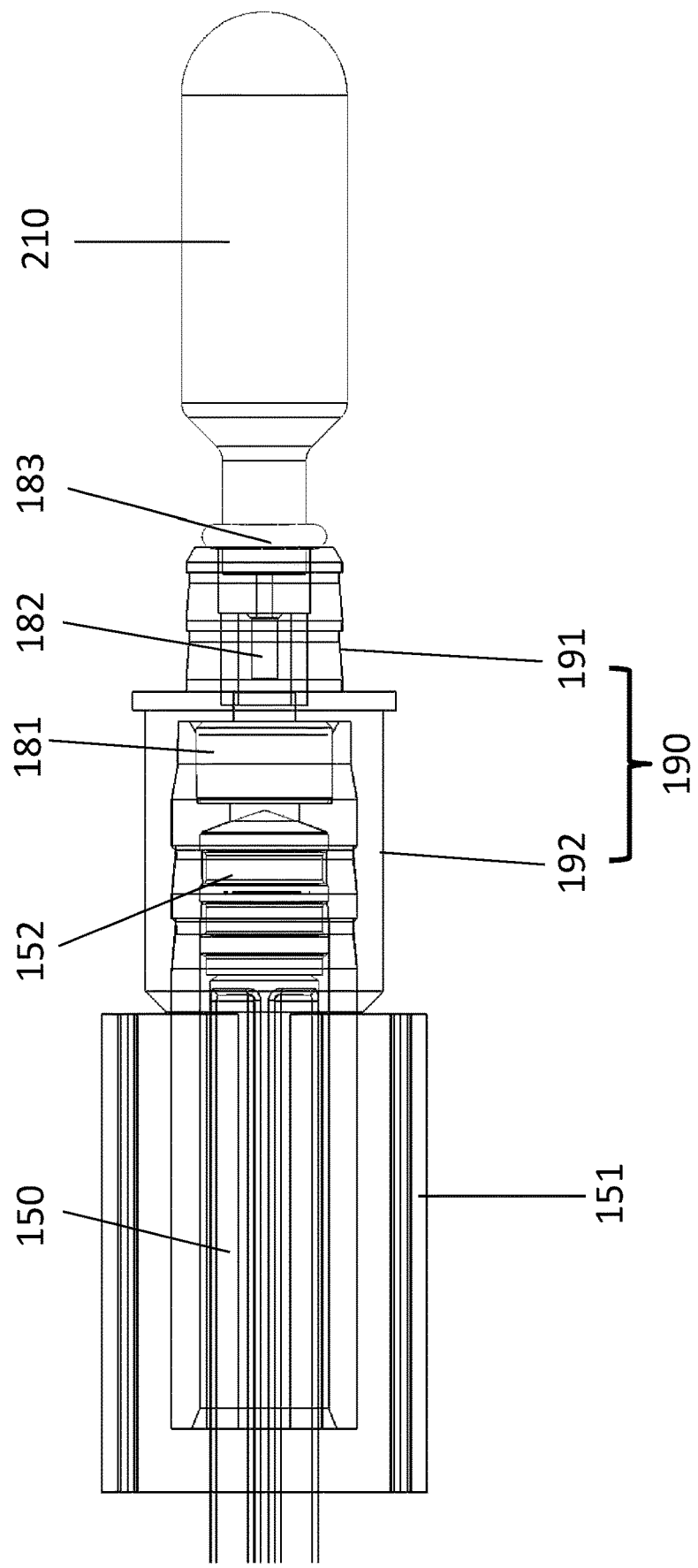
FIG. 9 shows a perspective view of the gas source, rupturer, second bracket, plunger carrier, and plunger.

FIG. 8 is a perspective view of the gas source 210 as well as the orifice 181 and rupturer 182 within the second bracket 190, wherein the second bracket 190 is made transparent to facilitate illustrating its inner structure. The rupturer 182 is fixed within a neck portion 191 of the second bracket 190 and ensures a gas-tight engagement with the neck portion 191. On the other hand, the orifice 181 is fixed within the main portion 192 of the second bracket 190 and also ensures a gas-tight engagement with the main portion 192. As illustrated in FIGS. 4, 8, and 9, the orifice 181 has two openings, one of the distal end to receive the pressurized gas exiting the rupturer 182 and the other on the proximal end for the pressurized gas to exit the orifice 181. The size of the openings can be adjusted to regulate the pressure of the gas generate while exiting the orifice 181. In this example, the opening on the orifice's 181 proximal end is smaller than that on the distal end, but it's not limited thereto. In other examples, the openings of the orifice 181 can be adjusted in order to regulate the pressure that the gas creates based on the need to push the plunger 150. Also, the orifice 181 regulates the flow rate at which the pressurized gas leaves the orifice 181 to push the plunger 150. In the present embodiment, the orifice 181 is configured to maintain the flow rate to be substantially constant to ensure that a constant force from the pressurized gas is pushing the plunger 150. In other embodiments, the orifice 181 can be configured to produce a varied flow rate in order to create different force output profile.

FIG. 9 shows a perspective view of the gas source 210, washer 183, rupturer 182, orifice 181, second bracket 190, plunger carrier 151, and plunger 150, wherein the plunger carrier 151 and second bracket 190 are made transparent to facilitate illustration of their inner structures. In FIG. 9, the seal on the gas source 210 had been pierced/ruptured by the rupturer 182 to release the pressurized gas within the gas source 210. The gas passes through the rupturer 182 and then enters the space within the second bracket 190 between the rupturer 182 and the orifice 181 within the neck portion of the plunger carrier 151. The opening on the distal end of the orifice 181 is configured to face the opening of the rupturer 182 so that the pressurized gas exiting the rupturer 182 can enter the orifice 181. The same pressurized gas then exits the orifice 181 through the opening on the proximal end to enter the space between the plunger stopper 152 and orifice 181. The pressurized gas then goes on to push the combination of plunger 151 and the plunger 150 in the proximal direction. In this example, one end of the plunger 150 is coupled with the plunger stopper 152 while the other end is configured to make contact with the piston/stopper within the syringe body 121 of syringe 120. Thus, when the pressurized pushes the plunger 150 to move in the proximal direction, the plunger 150 will make contact and then also pushes the piston/stopper 152 to move in the proximal direction. This proximal movement of the piston/stopper 152 then pushes the medicament within the syringe body 121 to pass through the needle 122 and finally enter the injection site for medicament delivery.

Additionally, even though a syringe 120 is described in this example embodiment of FIG. 2, any suitable type of medicament container may be used in the disclosed drug delivery device 100, such as a syringe, an ampoule, a cartridge, an enclosure, etc. Further, the medicament may be any suitable substance used for medical treatment. In an example embodiment, the medicament is epinephrine (commonly known as adrenaline).

In an example embodiment, the disclosed pneumatic power pack may be configured to propel the plunger with a constant or substantially constant force. An example drug delivery device having a pneumatic power pack configured to propel the plunger with a constant or substantially constant force is described with reference to FIGS. 1-9.

The pneumatic power pack 130 may propel the plunger within syringe 120 forward with any suitable substantially constant force. As mentioned herein, by the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Figure 10:
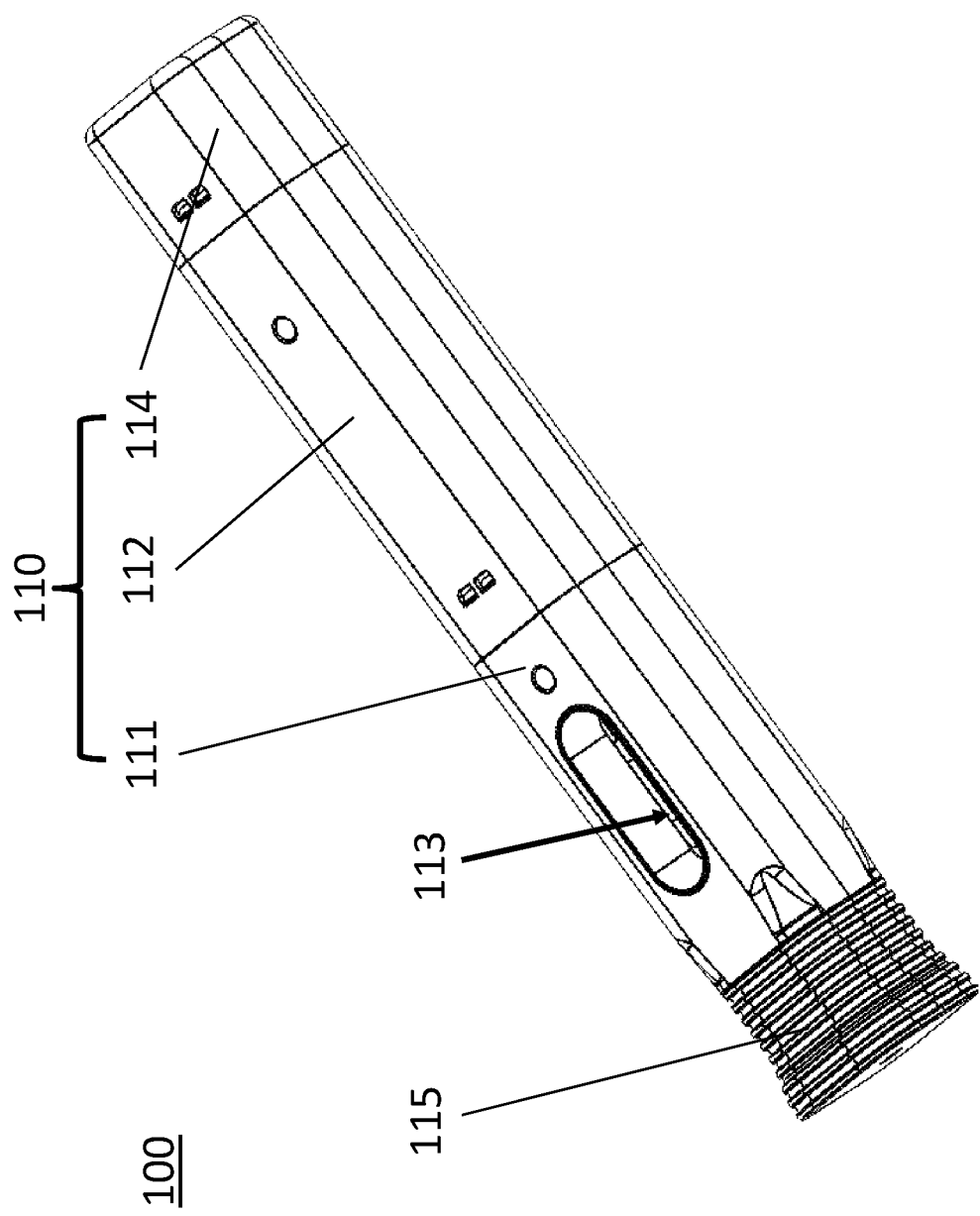
FIG. 10 shows a perspective view of an example medicament delivery device according to a second embodiment of the present disclosure.
Figure 11:
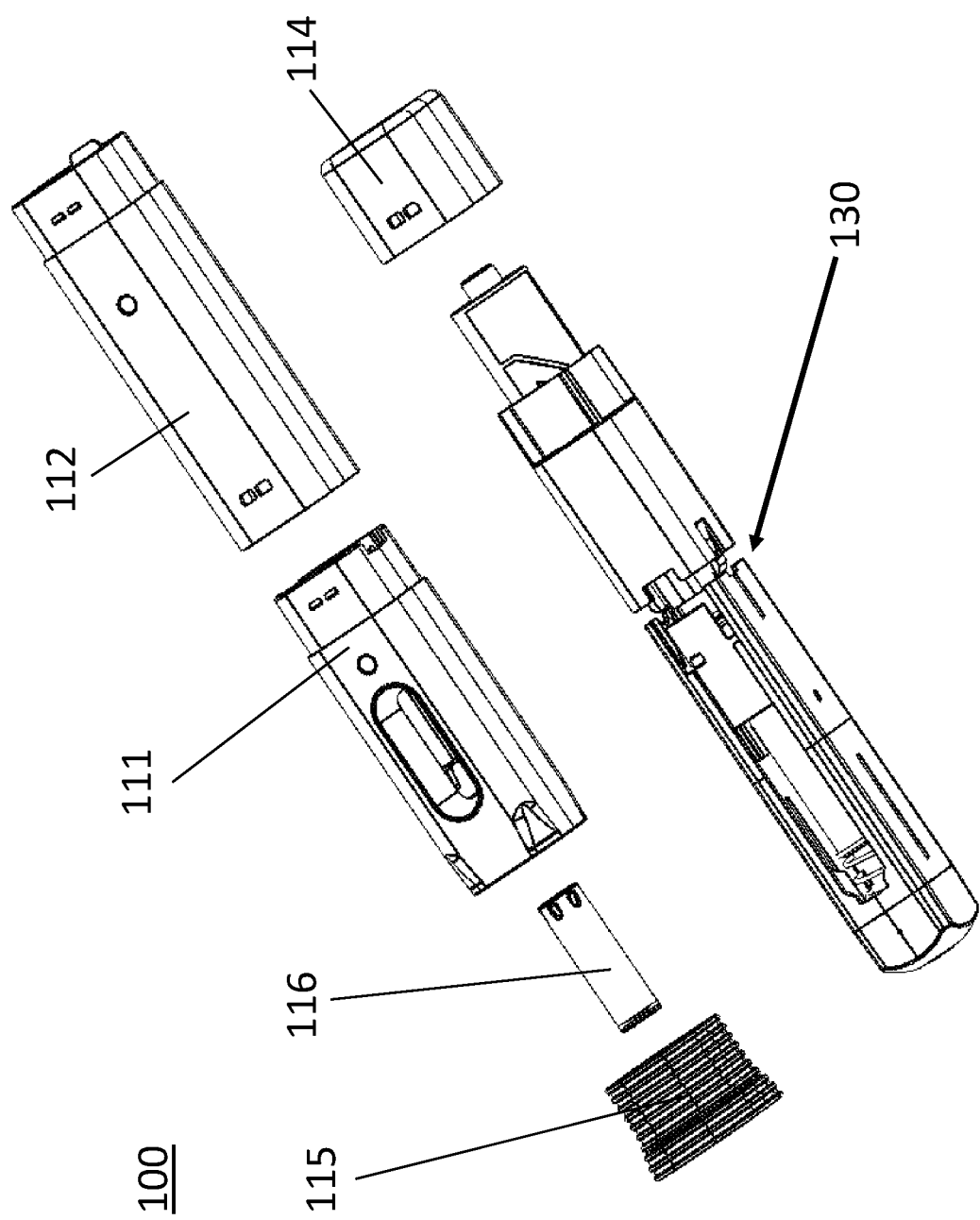
FIG. 11 shows an exploded view of an example medicament delivery device according to a second embodiment of the present disclosure.

FIGS. 10 and 11 illustrates another embodiment of the medicament delivery device of the present disclosure. In particular, FIG. 10 illustrates a drug delivery device 100 in an initial state prior to injection. Further, FIG. 11 illustrates an exploded view of the components of the drug delivery device 100 in the initial state prior to injection.

As seen in FIGS. 10 and 11, the drug delivery device 100 includes a main housing 110 having a first housing portion 111, a second housing portion 112, and a third housing portion 114. The first and second housing portions 111, 112 include corresponding engagement features for providing an engagement between the two housing portions 111, 112. Similarly, the second and third housing portions 112, 114 include corresponding engagement features for providing an engagement between the two housing portions 112, 114. In an example embodiment, during assembly of the drug delivery device 100, the housing portions 111, 112, 114 are irreversibly attached to one another. However, in other embodiments, the housing portions 111, 112, 114 can also be reversibly attached to each other. The drug delivery device 100 includes a cap 115 covering the proximal end of the first housing portion 111. The drug delivery device 100 also includes a needle shield remover 116 configured to couple with the cap 115 and for removing a needle shield covering the needle of a syringe enclosed by the pneumatic power pack 130.

The drug delivery device 100 also includes a pneumatic power pack 130 that is substantially identical to the one in the first embodiment. The components of the pneumatic power pack 130 in this embodiment are functionally identical to the ones of the pneumatic power pack 130 in the first embodiment. Thus, the components and their functions will not be explained in details.

Figure 12:
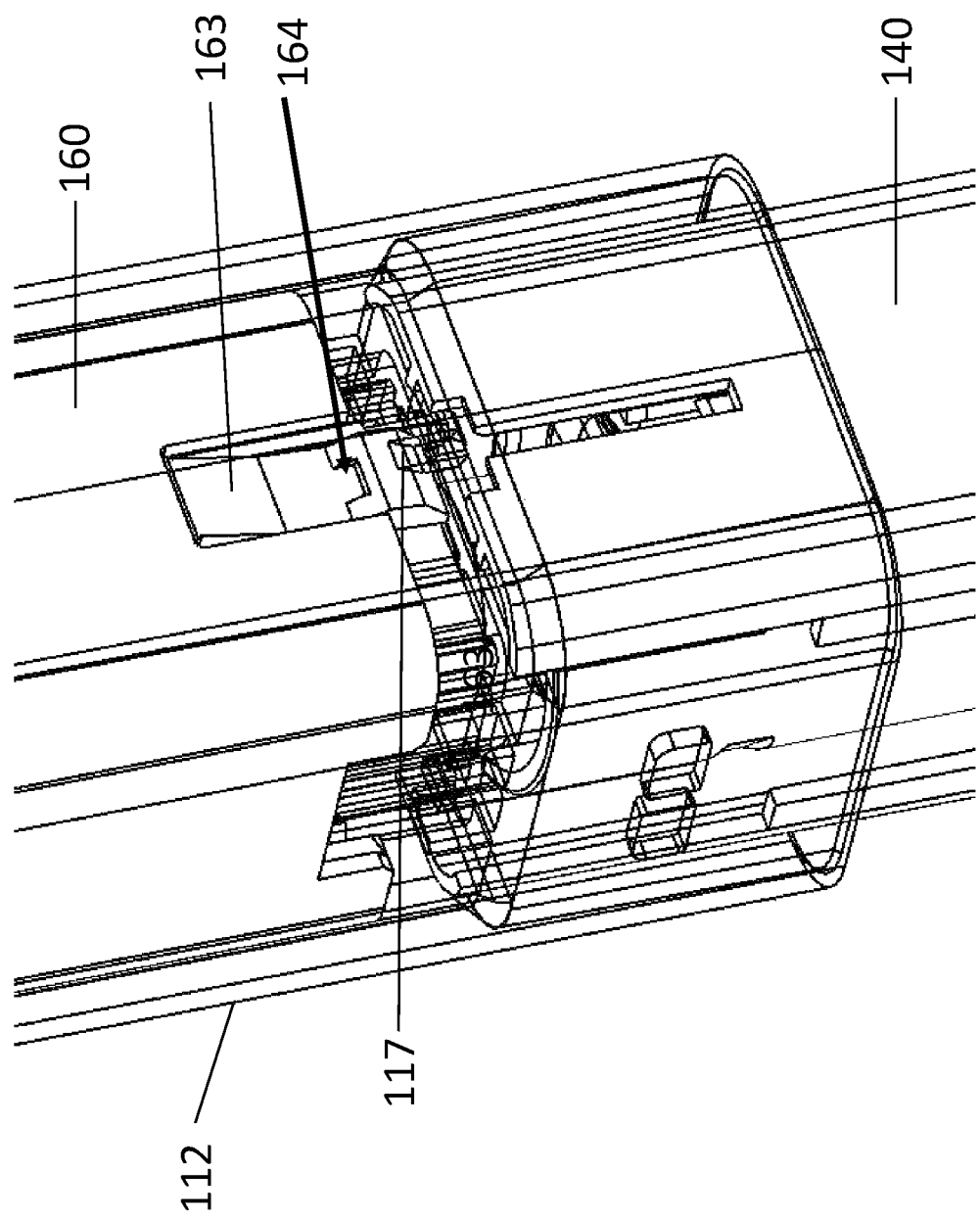
FIG. 12 shows a perspective view of the second housing portion, needle shield, and first rotator according to a second embodiment of the present disclosure.

FIG. 12 illustrates a perspective view of the medicament delivery device, wherein the first housing portion 111 is removed and the second housing portion 112 is made transparent to facilitate illustration. In the present embodiment, the first rotator 160 has at least one radially flexible tongue 163 disposed at the proximal end of the first rotator 160 and having a locking groove 164. On the other hand, the second housing portion 112 has a locking protrusion 117 disposed on the inner surface of the second housing portion 112 and corresponds to the locking groove 164. After the drug delivery device 100 is finally assembled, the locking protrusion 117 will be fitted in the locking groove 164 to engage the tongue 163. In this way, the locking protrusion 117 prevents the first rotator 160 from being moved in a distal direction, unless the tongue 163 flexes radially inward to disengage the locking protrusion 117. To decouple the tongue 163 from the locking protrusion 117, the user needs to press the needle shield 140 against the injection site to move the needle shield 140 in a distal direction. The needle shield 140 can then interact with the tongue 163 and force it to flex radially inward to disengage the locking protrusion 117. Once the disengagement is complete, the needle shield 140 can then abut the proximal end of the first rotator 160 and move it in a distal direction for the subsequent rotator of the second rotator 220.

Figure 13:
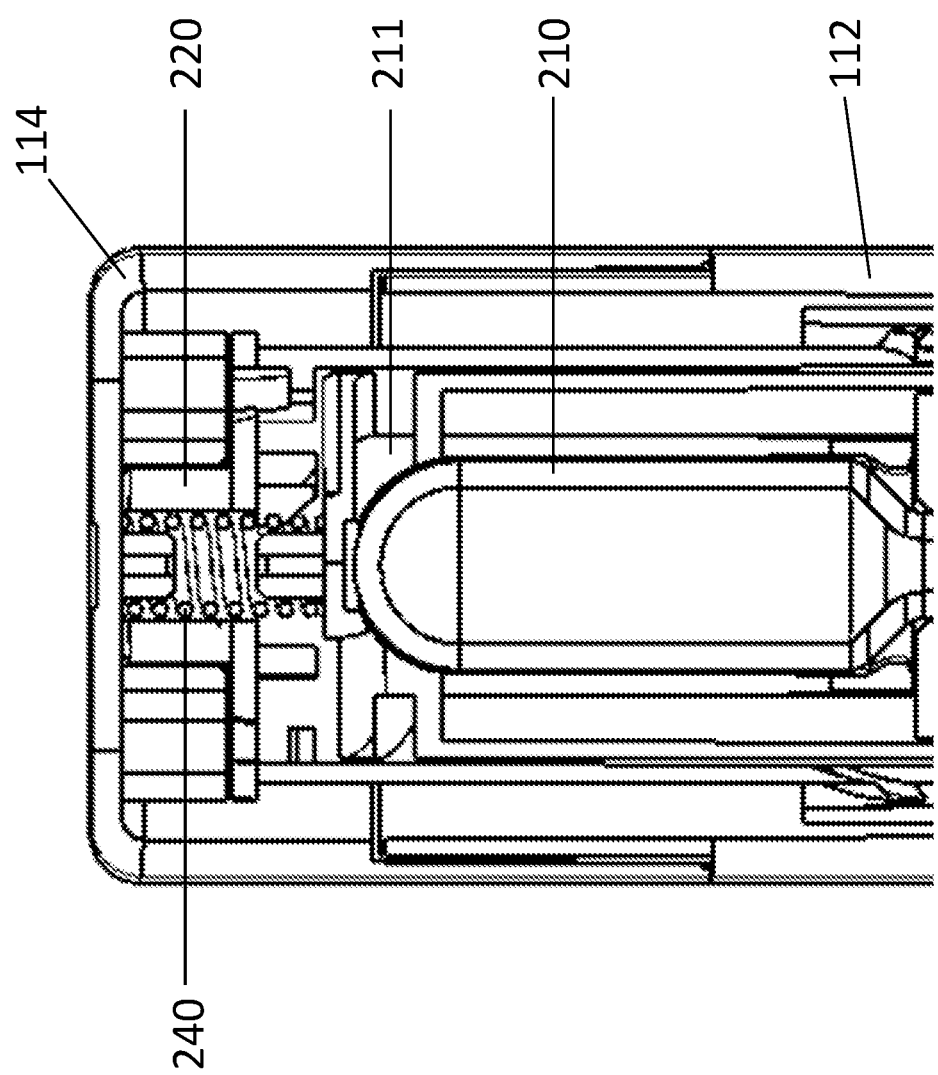
FIG. 13 shows a cross-section view of the distal end of the drug delivery device according to a second embodiment of the present disclosure.

FIG. 13 illustrates a cross-section view of the distal end of the drug delivery device 100. In the present embodiment, the drug delivery device 100 includes an auxiliary element 240 disposed between the third housing portion 114 and the gas source retainer 211. The auxiliary element 240 is configured to provide additional force needed to push the gas source retainer 211 in the proximal direction in order for the seal of the gas source 210 to be ruptured by the rupture (not illustrated) of the pneumatic power pack 130. In the present embodiment, the auxiliary element 240 is a spring, but can be other known element configured to provide forces to push the gas source retainer 211 in the proximal direction. Further, the drug delivery device 100 includes a first guide element 241 disposed on the inner surface of third housing portion 114 and a second guide element 2'12 disposed on the gas source retainer 211 for making sure that the axis of the auxiliary element 240 is longitudinal and parallel to that of the drug delivery device 100.

In an example embodiment, the substantially constant force at which the plunger is propelled is any substantially constant force falling in the range of forces between 10N and 100N+−15N. Further, as used herein, a substantially constant force of X Newtons means any force in the range of 10N and 100N+−15N.

Beneficially, the disclosed pneumatic power pack provides a cost effective means for propelling a plunger forward in an automatic injection device. Further, embodiments of the disclosed pneumatic power pack also provide a low-cost means for propelling the plunger forward at a substantially constant force. Therefore, the disclosed pneumatic power pack may help to reduce the cost of manufacturing automatic injection devices.

In the examples shown in the Figures, the drug delivery devices 100 is configured to inject a non-variable dose of medicament. However, in other embodiments, the drug delivery device could be configured to allow the user to select a variable single dose. For instance, in an example embodiment, the user is able to select two different dose values, three different dose values, four different dose values, and so forth.

In the Figures, various engagement features for are shown for providing an engagement between one or more components of the drug delivery device. The engagement features may be any suitable connecting mechanism such as a snap lock, a snap fit, form fit, a bayonet, lure lock, threads or combination of these designs. Other designs are possible as well.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. A pneumatic power pack, comprising:
   a pressurized gas container storing pressurized gas;
   a rupturer having a sharp end positioned adjacent the pressurized gas container;
   a needle shield having a proximal end and a distal end;
   a first rotator having a proximal end and a distal end, wherein the distal end of the needle shield is positioned adjacent the proximal end of the first rotator; and
   a second rotator coupled with the first rotator and the gas container,
   wherein, in response to the proximal end of the needle shield contacting an injection site, the first rotator is configured to move in a distal direction, and
   wherein the movement of the first rotator in the distal direction causes a rotation of the second rotator which then drives the pressurized gas container towards the sharp end of the rupturer to thereby release the pressurized gas.

2. The pneumatic power pack of claim 1, further comprising:
   a retainer coupled with the second rotator, wherein the gas container is arranged in the retainer, the movement of the first rotator in the distal direction causes the rotation of the second rotator which then drives the retainer and the pressurized gas container towards the sharp end of the rupturer.

3. The pneumatic power pack of claim 2, further comprising:

a first bracket coupling with the retainer, wherein the coupling between the first bracket and retainer transforms a movement of the retainer from rotational to longitudinal.

4. The pneumatic power pack of claim 3, wherein the first bracket has a passageway for accommodating the rupturer and at least part of the pressurized gas container such that a flow of the pressurized gas travels from the pressurized gas container through the rupturer and exits from the passageway.

5. The pneumatic power pack of claim 4, further comprising:
a second bracket and a valve disposed in the second bracket, wherein the valve receives a flow of gas exiting the passageway of the first bracket.

6. The pneumatic power pack of claim 2, wherein the second rotator includes a second protrusion and the retainer includes a slant slope configured to engage the second protrusion, and wherein the second protrusion is configured to interact with the slant slope during the rotation of the second rotator to drive the pressurized gas container.

7. The pneumatic power pack of claim 6, wherein the second rotator has a first fixing member and the retainer has a second fixing member configured to engage the first fixing member to maintain a position of the second rotator before being rotated by the movement of the first rotator in the distal direction.

8. The pneumatic power pack of claim 1, wherein the first rotator includes a protrusion and the second rotator includes a trough configured to engage the protrusion, wherein the protrusion is configured to interact with the trough during the movement of the first rotator in the distal direction to rotate the second rotator.

9. The pneumatic power pack of claim 8, wherein the protrusion is arranged on an inner surface of the first rotator, and wherein the trough is arranged on an outer surface of the second rotator.

10. The pneumatic power pack of claim 8, wherein the protrusion is arranged on an outer surface of the first rotator, and wherein the trough is arranged on an inner surface of the second rotator.

11. A drug delivery device comprising:
a main housing;
a medicament container including a stopper and a medicament; and
the pneumatic power pack of claim 1, wherein the pneumatic power pack further includes a plunger configured to engage the stopper and be movable by the pressurized gas in a proximal direction.

* * * * *